(12) United States Patent
McClure et al.

(10) Patent No.: US 10,160,987 B2
(45) Date of Patent: Dec. 25, 2018

(54) COMPOSITION AND METHOD FOR PROCESSING DNA

(71) Applicants: Rebecca F. McClure, Sudbury (CA); Tyler P. Kirwan, Hanmer (CA)

(72) Inventors: Rebecca F. McClure, Sudbury (CA); Tyler P. Kirwan, Hanmer (CA)

( * ) Notice: Subject to any disclaimer, the term of this patent is extended or adjusted under 35 U.S.C. 154(b) by 379 days.

(21) Appl. No.: 15/092,917

(22) Filed: Apr. 7, 2016

(65) Prior Publication Data

US 2017/0292137 A1 Oct. 12, 2017

(51) Int. Cl.
| | | |
|---|---|---|
| *C12Q 1/68* | (2018.01) |
| *C12P 19/34* | (2006.01) |
| *C12Q 1/6806* | (2018.01) |
| *C12Q 1/6874* | (2018.01) |

(52) U.S. Cl.
CPC ............ *C12P 19/34* (2013.01); *C12Q 1/6806* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 5,035,996 A | 7/1991 | Hartley | |
| 5,229,283 A | 7/1993 | Berninger | |
| 6,046,039 A | 4/2000 | Wong | |
| 6,090,553 A | 7/2000 | Matson | |
| 6,190,865 B1* | 2/2001 | Jendrisak | ............. C12Q 1/6848 |
| | | | 435/6.12 |
| 6,762,022 B2 | 7/2004 | Makarov et al. | |
| 7,851,192 B2 | 12/2010 | Guan et al. | |
| 8,058,414 B2 | 11/2011 | Menchen et al. | |
| 8,603,792 B2 | 12/2013 | Nikiforov et al. | |
| 8,673,560 B2 | 3/2014 | Leamon et al. | |
| 8,703,462 B2 | 4/2014 | Hsieh et al. | |
| 8,728,728 B2 | 5/2014 | Leamon et al. | |
| 8,728,736 B2 | 5/2014 | Leamon et al. | |
| 2004/0067559 A1 | 4/2004 | McCarthy et al. | |
| 2004/0086890 A1* | 5/2004 | Sorge | ..................... C07H 21/04 |
| | | | 435/6.11 |
| 2010/0112595 A1 | 5/2010 | Liu et al. | |
| 2010/0120157 A1 | 5/2010 | Zon | |
| 2011/0014657 A1 | 1/2011 | Rigatti et al. | |

(Continued)

FOREIGN PATENT DOCUMENTS

| | | |
|---|---|---|
| WO | WO 2007/046854 | 4/2007 |
| WO | WO 2012/149438 | 11/2012 |
| WO | WO 2014/105246 | 7/2014 |

OTHER PUBLICATIONS

Guan et al., "A Single catalytic domain of the junction-resolving enzyme T7 endonuclease I is a non-specific nicking endonuclease," Nucleic Acids Research, vol. 33, No. 19, pp. 6225-6234. (Year: 2005).*

(Continued)

*Primary Examiner* — Young J Kim
(74) *Attorney, Agent, or Firm* — Brinks Gilson & Lione (57) ABSTRACT

A method of cleaving DNA molecules into smaller fragments by the creation of "cleavage trigger sites" followed by enzymatic processing. In some embodiments the "cleavage trigger sites" are created by the incorporation of nucleotides having uracil bases into a DNA molecule and processing with uracil DNA glycosylase, endonuclease IV and T7 endonuclease I.

10 Claims, 3 Drawing Sheets

(56) References Cited

U.S. PATENT DOCUMENTS

| | | |
|---|---|---|
| 2011/0033854 A1 | 2/2011 | Drmanac et al. |
| 2012/0191363 A1 | 7/2012 | McKernan et al. |
| 2012/0295819 A1 | 11/2012 | Leamon et al. |
| 2014/0031261 A1 | 1/2014 | Goryshin et al. |
| 2014/0120539 A1 | 5/2014 | Tanner et al. |
| 2015/0226671 A1* | 8/2015 | Huang .................... C12Q 1/34 435/6.1 |

OTHER PUBLICATIONS

Canadian Office Action dated Mar. 5, 2018.

\* cited by examiner

COMPOSITION AND METHOD FOR PROCESSING DNA

FIELD OF THE INVENTION

This invention relates to compositions and methods for processing DNA or RNA complementary DNA (cDNA) molecules (hereafter may be referred to together as DNA/cDNA). Particularly, the invention relates to a process in which a unique DNA fragment is created such that when it is bound to exact or quasi sequence-complementary DNA/cDNA, one or more "cleavage trigger sites" (hereafter may be referred to as triggers) are created that are subsequently cleaved by one or more enzymes. The resulting fragmented DNA/cDNA is suitable for use in a variety of further applications (for example; DNA sequencing, including high-throughput sequencing).

BACKGROUND

Manipulation of nucleic acids has been used for decades in numerous applications in a variety of fields of biological science. One of the fundamental processes that has enabled the diverse utility of nucleic acid manipulation is the ability to cleave nucleic acid. Typically, cleavage of DNA/cDNA is mediated by restriction endonucleases, which are a class of enzymes that recognize short (6-15 bp) specific sequences of DNA/cDNA called restriction sites, which must be present in the DNA/cDNA being cleaved. Cleaving DNA/cDNA at a sequence-specific location typically requires that there be a commercially available restriction endonuclease that is specific for the sequence in the desired cleavage location and that this enzyme naturally cleaves in the exact base-pair location within the recognition sequence that is desired. Because restriction endonucleases cleave all compatible recognition sites present, their utility is limited if the recognition site is present in locations where cleavage is not desired. Thus, the usefulness of restriction enzyme mediated cleavage is limited in emerging technologies that are high-throughput, have complex template, or have regions where the exact template sequence is unknown. It has been a challenge to develop a robust, flexible and cost-effective method for highly specific targeted cleavage of nucleic acids into fragments that are optimal and agnostic for downstream applications.

SUMMARY OF THE INVENTION

The disclosure provides a method/technique for DNA/cDNA cleavage through modifications that create unique regions of DNA/cDNA containing cleavage trigger sites. Different approaches for the method are presented, but in each, a unique fragment of DNA is created in such a manner that, when bound to an exact or quasi sequence-complementary DNA/cDNA region, cleavage trigger sites are created that are subsequently cleaved by enzymatic reactions. The type of DNA fragment created, how it is created, and the number and type of enzymes used for cleavage may differ depending on the anticipated downstream application. This method of DNA/cDNA cleavage is distinct from current cleavage methods (including restriction endonucleases), allows for precise control over DNA/cDNA cleavage and is adaptable to emerging technologies.

In one embodiment, the present disclosure provides a method of processing DNA molecules. The method includes binding (or annealing) a single-stranded DNA molecule to a template DNA molecule to form a duplex DNA that includes a cleavage trigger site, the trigger being at least one of a non-canonical nucleotide, a modified nucleotide, and a structural trigger. In one step, the duplex DNA is treated with a DNA-modifying enzyme capable of recognizing the trigger and removing the trigger by a catalytic reaction, resulting in the creation of an intermediate product. In another step, the intermediate product is nicked at the site where the trigger was removed to create a nick. In another step, the template DNA molecule is cut opposite the nick to create at least one DNA fragment.

In one embodiment, the present disclosure provides a method of processing DNA molecules. The method includes the steps of creating a reaction mixture by binding or annealing at least one uracil-containing oligonucleotide to a precursor DNA containing a target sequence to be isolated and purified, the precursor DNA being a single-stranded DNA, each of the at least one uracil-containing oligonucleotides binding (or annealing) in sequence-specific fashion to a region adjacent the target sequence to form a uracil-containing duplex; treating the uracil-containing duplex with a first enzyme to remove the uracil base and to create an apyrimidinic site to form an apyrimidinic site-containing duplex; treating the apyrimidinic site-containing duplex with a second enzyme to create a nick at the apyrimidinic site to form a partial duplex, the precursor being intact opposite the nick; and treating the partial duplex with a third enzyme to cut the precursor DNA opposite the nicked strand; and optionally isolating the target sequence by a physical separation method.

In another embodiment, the present disclosure provides another method of processing DNA. The method includes steps of performing a polymerase chain reaction using a polymerase, at least one DNA primer, and a nucleotide mixture, on a template DNA containing a target sequence, the nucleotide mixture comprising a uracil-containing nucleotide, the polymerase being capable of incorporating uracil into a product DNA, each of the at least one DNA primers having sequence homology to a region adjacent the target sequence of the template DNA, the polymerase chain reaction forming a uracil-containing duplex; treating the uracil-containing duplex with a first enzyme to remove the uracil base and to create an apyrimidinic site to form an apyrimidinic site-containing duplex; treating the apyrimidinic site-containing duplex with a second enzyme to create a nick at the apyrimidinic site to form a partial duplex, the precursor being intact opposite the nick; treating the partial duplex with a third enzyme to cut the DNA strand opposite the nicked strand; and optionally isolating the target sequence by a physical separation method.

BRIEF DESCRIPTION OF THE FIGURES

FIG. 3 is an Agilent 2100 Bioanalyzer e-gel (FIG. 3a) and electropherogram (FIG. 3b) on which products of the present invention have been run.

DETAILED DESCRIPTION

It will be appreciated that drawings in this disclosure are not necessarily to scale, with some components enlarged relative to their actual size in order to show detail. The terms "substantially," "about," or derivatives thereof will be understood to mean significantly, effectively, or in large part.

Disclosed herein is a method for targeted cleavage of template DNA/cDNA for any purpose. The method is a process in which a unique DNA fragment is created such that when it is bound to an exact or quasi sequence-complementary DNA/cDNA fragment (template), one or more "cleavage trigger sites" are created that are subsequently cleaved by one or more enzymes. As used herein, a "trigger" is a structure within a double-stranded DNA molecule that provides for recognition and processing by an enzyme. For example, the trigger may be formed as a consequence of incorporating a "trigger nucleotide" into a strand of DNA. One such trigger nucleotide may be, for example, deoxyuridine. A deoxyuridine in duplex DNA serves as a structural cue for recognition by uracil DNA glycosylase, which then processes the DNA molecule by cleaving the uracil base, generating an abasic site. Further examples of trigger nucleotides can be found in Table 1.

Trigger nucleotides may fall into one of two groups: non-canonical nucleotides and modified nucleotides. A non-canonical nucleotide is a nucleotide that may be incorporated into DNA or RNA in nature, but does not have a base which is among the four canonical DNA bases: adenine, thymine, cytosine, and guanine. Therefore, a nucleotide bearing a uracil base is considered a trigger in this context. A modified nucleotide is a nucleotide which has a base that bears a chemical modification, or that forms a stable abasic site, but may nonetheless be incorporated into a strand of DNA. Examples of modified nucleotides include, but are not limited to, 3-methyladenine and 7-methylguanine.

In some cases, the trigger may be a structural trigger. When the trigger is a structural trigger, the presence of a trigger may not be evident when the strands are separated; for instance, if a trigger is formed by a base-pairing mismatch of one or more nucleotide pairs, analysis of one of the separated strands in isolation would not necessarily indicate that a trigger is present. Examples of structural triggers are listed in Table 1. It is noted that sequences with perfect Watson-Crick base pairing, such as recognition sites for sequence-specific restriction endonucleases are not considered to contain a trigger.

The fragmented template DNA/cDNA resulting from such a cleavage scheme is suitable for use in a variety of applications. Applications include, but are not limited to, DNA sequencing, including high-throughput sequencing (variably described by alternate terms such as deep sequencing, next-generation sequencing, next, next generation sequencing etc).

FIG. 1 is a broad illustration of one embodiment. In this embodiment, sequence-specific DNA fragments are produced to create the trigger site(s). In this example, the trigger site is created by a trigger nucleotide, deoxyuridine. Deoxyuridine is a nucleotide which has uracil as its base. Therefore, deoxyuridine may be considered to be a component of a "uracil-containing" DNA molecule.

The produced DNA fragment is bound (or annealed) to the template DNA/cDNA thereby creating the trigger site. In one embodiment, the binding is accomplished by base-pairing such that the single-stranded molecules come together to form a duplex which is held together by hydrogen bonding, rather than formation of covalent bonds. The trigger-containing DNA can then be cleaved by an enzyme mixture in which the enzymes work sequentially. Depending on the exact nature of the cleavage desired, variations of this example may be used. The figure shows examples using one (a) or two (b) trigger-forming fragments to separately cleave both strands of dsDNA template. Strands 101/102 of template DNA/cDNA are subjected to heat denaturation 110 to form single-stranded precursor DNA, and are bound in a sequence-specific fashion by the trigger-forming DNA fragment (FIG. 1a) or fragments (FIG. 1b) 111 that have been created to contain deoxyuridine(s) 112 (that is, uracil-containing oligonucleotides), resulting in the formation of a uracil-containing duplex DNA. In one variation (a) a single trigger-forming fragment is used and in the second variation (b) two trigger-forming fragments are used. These variations can be used to produce different configurations of the cleavage site following enzymatic processing. Produced trigger-forming DNA fragments around 20 nucleotides long are particularly considered for this application, but fragments as short as 5 or 6 nucleotides, and as long as a hundred, or several hundred, or more than a thousand, including several thousand nucleotides, are envisioned as being useful for applications in accordance with the principles of this disclosure.

Figure 1A:
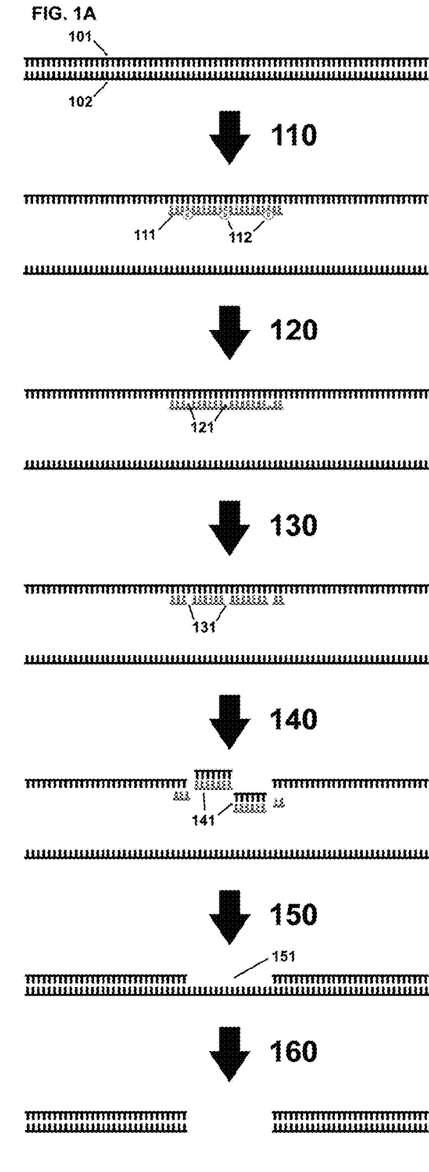
FIGS. 1a and 1b provide a schematic view of an embodiment of a method of DNA treatment according to one embodiment of the present disclosure.
Figure 1B:
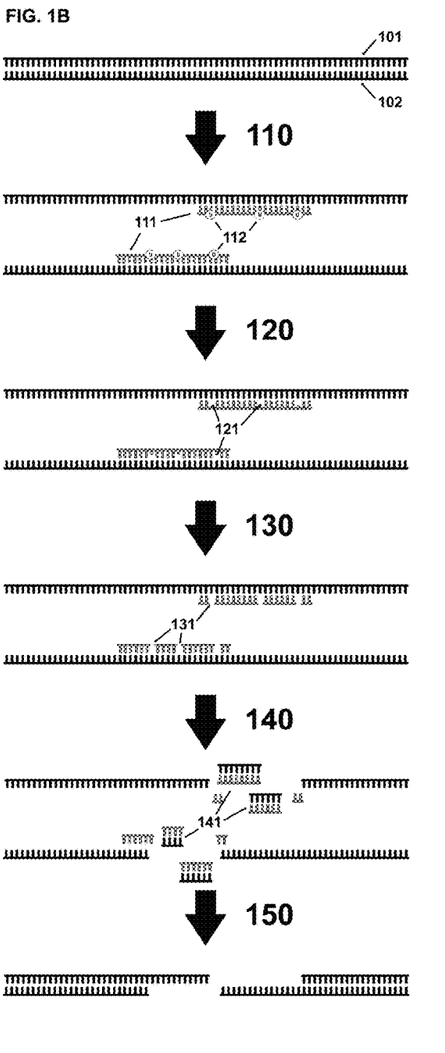

In the example illustrated, the template DNA 101/102 may be DNA/cDNA obtained in any way from any species. Templates may include, but are not limited to, genomic DNA in any form, artificial DNA/cDNA of any length including plasmid DNA, PCR products, modified DNA, synthetic nucleic acid and the like. The target sequences within the DNA template that are complementary to the trigger-forming fragment may be any sequence including, but not limited to, those within the introns and exons of genes.

In the example shown, deoxyuridine 112 is used as a trigger nucleotide to create the cleavage trigger site. However, it is to be understood that cleavage trigger sites can be created by use of any nucleotide(s), modified nucleotide(s), nucleotide analog(s), or sequences that form secondary structures that deviate from the structure of perfectly base-paired DNA upon annealing to template. It will be appreciated that because of the diversity of potential trigger sites, any number of enzymes can be used separately or in combination to generate breakages in template at locations identified by trigger forming fragments (See Table 1). It will be appreciated that the triggers listed in Table 1 may be the listed trigger, or derivatives thereof, and that the triggers can take the form of trigger nucleotides or triggering double-stranded DNA structures.

TABLE 1

| TRIGGER | TRIGGER TYPE | ENZYME MIX |
| --- | --- | --- |
| Deoxyuridine | Non-canonical nucleotide | UDG or Afu-UDG; plus Endonuclease IV or Tth Endonuclease IV; plus T7 Endo1 or S1 nuclease or mung bean nuclease |
| 1',2'-dideoxyribose (stable abasic site) | Modified nucleotide | Endonuclease IV or Tth Endonuclease IV; plus T7 Endo1 or S1 nuclease or mung bean nuclease |
| Deoxyinosine | Non-canonical nucleotide | Endonuclease V (optionally with T7 Endonuclease 1) |
| Deoxyuridine | Non-canonical nucleotide | Endonuclease V (optionally with T7 Endonuclease 1) |
| Mismatched DNA/ other secondary structures | Structural | Endonuclease V (optionally with T7 Endonuclease 1) |

TABLE 1-continued

| TRIGGER | TRIGGER TYPE | ENZYME MIX |
|---|---|---|
| Deoxyinosine | Non-canonical nucleotide | hAAG; plus Endonuclease IV or Tth Endonuclease IV; plus T7 Endo1 or S1 nuclease or mung bean nuclease |
| 3-methyladenine | Modified nucleotide | hAAG; plus Endonuclease IV or Tth Endonuclease IV; plus T7 Endo1 or S1 nuclease or mung bean nuclease |
| 7-methylguanine | Modified nucleotide | hAAG; plus Endonuclease IV or Tth Endonuclease IV; plus T7 Endo1 or S1 nuclease or mung bean nuclease |
| 1,N6-ethenoadenine | Modified nucleotide | hAAG; plus Endonuclease IV or Tth Endonuclease IV; plus T7 Endo1 or S1 nuclease or mung bean nuclease |
| Hypoxanthine | Non-canonical nucleotide | hAAG; plus Endonuclease IV or Tth Endonuclease IV; plus T7 Endo1 or S1 nuclease or mung bean nuclease |
| Cruciform DNA structures | Structural | T7 Endonuclease 1 |
| Small insertions or deletion (INDEL) | Structural | T7 Endonuclease 1 |

In a first enzymatic step 120, the trigger-containing duplex DNA is exposed to an enzyme that excises the trigger nucleotide. In the example shown, deoxyuridine is the trigger nucleotide such that an appropriate first DNA-modifying enzyme is uracil DNA glycosylase (UDG). UDG catalyzes the release of free uracil from uracil-containing DNA by binding to the DNA backbone, flipping the base out of the helical structure of the DNA strand, and removing the base by cleaving the glycosidic bond between the base and the sugar if the base is able to intercalate into a specificity site of the enzyme. After UDG cuts, an abasic (specifically, apyrimidinic (AP)) site 121 is created at the position(s) that deoxyuridine 112 previously occupied in the oligonucleotide probe(s) 111, with the backbone left intact. This yields an abasic site, or apyrimidinic site-containing duplex DNA, referred to here as an intermediate product. The method can also be performed by substituting any enzyme for UDG that has similar function as indicated in Table 1.

In a second enzymatic step 130, the duplex DNA containing abasic sites 121, or intermediate product, is treated with a second DNA-modifying enzyme; in this case, a nicking enzyme. In the example shown, the enzyme may be endonuclease IV (Endo IV), which recognizes apurinic and apyrmidinic sites in double-stranded DNA (dsDNA) duplexes and cleaves the phosphodiester bond of the sugar-phosphate backbone on the 5' side of the abasic lesion 131. The DNA duplexes remain intact, as there is no effect on base pairing, but the backbone is nicked 131 after Endo IV treatment. Depending on the number of deoxyuridine nucleotides that had initially been present, there may be a single nick, or numerous nicks per duplex. The method can also be performed by substituting any enzyme for Endo IV that has similar function (See Table 1).

In enzymatic step 140, the nicked duplex template is treated with a third DNA-modifying enzyme that will nick the backbone of the original precursor (or template) DNA on the opposite strand from the previous nick 131. A second nick will release duplex DNA on either side of the nick, resulting in the formation of DNA fragments. In the example shown, this enzyme may be T7 Endonuclease I (T7 Endo I). T7 Endo I generally recognizes and cleaves a variety of structures, including DNA with imperfect base pairing, cruciform DNA structures, Holliday junctions, heteroduplex DNA, and double-stranded DNA. Cleavage does not necessarily occur at an exact location directly opposite the Endo IV nick. The method can also be performed by substituting any enzyme for T7 Endo I that has similar function (See Table 1). At this point, the trigger-forming DNA fragments 111, which were used to specify the sequence targeted for cleavage, have been degraded to very small molecules 141, and the reannealing of the strands 101/102 to one another is thermodynamically favored 150.

In the variation using trigger-forming fragments that do not target both strands of a homologous region of double stranded template DNA/cDNA (FIG. 1*a*), a final enzyme such as Endonuclease TT or the like (See Table 1) is used to cleave the resultant single strand 151 for full, double-strand cleavage of the template 160.

It will be appreciated that the enzymes used for DNA/cDNA cleavage can be added consecutively, or they may be added simultaneously to the reaction mixture, in which case, they will process consecutively as enzymatic reactions create DNA structures to serve as substrates for further reactions.

In one embodiment of the method, the trigger-forming DNA fragment location design determines exactly where the template will be cleaved and is sequence-specific. Although the figure shows the method with only a single region illustrated, for each variation, typically many trigger-forming fragments targeting a variety of different regions would be created and used simultaneously to cleave the template at multiple locations.

Following the cutting step, the desired DNA fragments may be amenable to downstream applications in their current state or first purified away from contaminating DNA and enzymes in a purification step. The duplex fragments may be purified away from the remaining DNA using a size-exclusion technique. A silica resin, which binds DNA in a sequence-independent manner, may be employed. In such a purification scheme, high concentrations of chaotropic salts are added to form a mixture, and this mixture is placed into contact with a silica resin. The silica resin may be in the form of a powder, packed into a column, provided in a commercially-available spin column, or in any other format. Large DNA molecules such as for example genomic DNA (gDNA) bind so tightly to the silica resin that they are retained even under the low-ionic strength conditions that allow the cut fragments to elute. Thus, when the precursor DNA is gDNA, the eluent will contain the fragments. The fragments may also be purified following agarose or acrylamide gel electrophoresis rather than binding to silica. Alternatively, a magnetic bead-based purification approach may be used, or the DNA may be purified using sequence-specific, immobilized capture probes.

Figure 2:
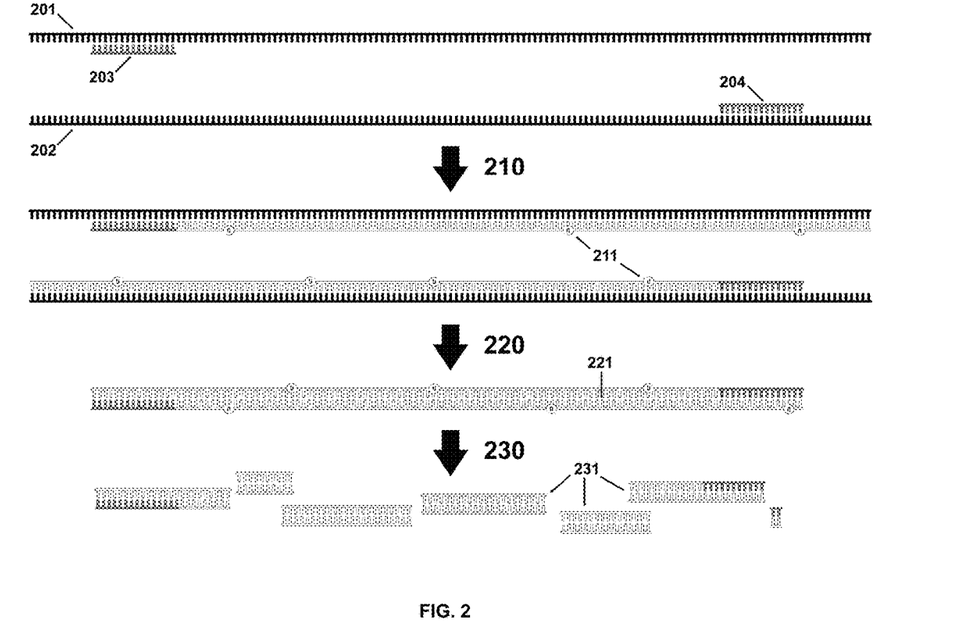
FIG. 2 contains a schematic view of another embodiment of a DNA treatment method.

FIG. 2 is a broad illustration of another embodiment of the present disclosure in which cleavage trigger sites are formed by direct incorporation of a trigger nucleotide into one or both strands of template, removing the need for a hybridization step as in the prior embodiment illustrated in FIG. 1. Two DNA fragments containing trigger nucleotides are created using polymerase chain reaction (PCR). In this example, the trigger nucleotide is deoxyuridine, which is incorporated directly during the PCR reaction. The trigger, therefore, is the uracil-containing region of the duplex. The PCR product is subsequently cleaved by an enzyme mixture in which the enzymes work sequentially.

It is to be understood that cleavage trigger sites can be any nucleotide(s), modified nucleotide(s), or nucleotide analog(s) that can be incorporated into a strand of nucleic acid being synthesized by a polymerase, reverse transcriptase, or the like. The resulting synthesized strands of DNA contain a small percentage 5%) of trigger nucleotide sites so that subsequent enzymatic digestion, as described for the first embodiment, produces fragments of template DNA/cDNA of a size suitable for the desired downstream application. In the example shown, 2'-deoxyuridine 5'-triphosphate (dUTP) is incorporated as the trigger nucleotide. DNA/cDNA, which includes strands 201 and 202, is amplified using primers 203 and 204 and any enzyme that can incorporate dUTP or other designated trigger nucleotide (See Table 1). In the example shown, the nucleotide mixture used in the PCR reaction has a fraction of deoxythymidine triphosphate (dTTP) replaced by dUTP. This allows for a semi-random substitution of deoxyuridine 211 where thymidine would otherwise naturally occur and targets the resulting double stranded PCR product 221 for enzymatic processing 230. The average size of the final cleaved fragments 231 can be controlled by adjusting dTTP:dUTP ratio, with more dUTP translating to smaller fragments, and more dTTP producing larger fragments. The ratio of dTTP:dUTP may be 1:1 or lower in one embodiment, or 9999:1 or higher in another embodiment, or any value between 1:1 and 9999:1 in another embodiment.

It will be appreciated that although only two primers (203 and 204) are illustrated, this method allows for multiple primers targeting one or more locations within the template to be multiplexed per PCR reaction.

In another embodiment, a kit for DNA processing is disclosed. A kit may include any or all of the three processing enzymes UDG, Endo IV, and T7 Endo I in order to allow a user to degrade DNA in the manner described herein. In one embodiment, the enzymes are provided individually. In another embodiment, the enzymes may be provided as a single mixture. In another embodiment, the kit may include other enzymes, together or separately, as indicated by Table 1, in order to treat substrates generated by a particular method. In still another embodiment, the kit may be provided not only with the processing enzymes, but with a polymerase, or a nucleotide mix, or both, if a PCR methodology is preferred. In an embodiment wherein a non-canonical nucleotide or a modified nucleotide is incorporated to form the trigger, the nucleotide may be provided in the kit.

A method in accordance with the principles of the present disclosure may be useful for a variety of downstream applications. Some applications would allow isolation of selected regions of DNA from surrounding DNA for further analysis. This could be either through positive selection of desired areas of DNA/cDNA or through negative selection by degradation of non-desirable regions of DNA/cDNA. Application for Positive Selection of Desired Areas of DNA/cDNA for High-Throughput Sequencing (HTPS).

The HTPS technique uses fragments of DNA (called a sequencing library), and libraries containing long fragments are particularly desirable for reliable analysis of DNA variants.

The method as described in FIG. 1 can allow for large fragments to be generated from specified areas of interest (for example designated gene exons), which is difficult to do using current fragment creation techniques. PCR-based library creation methods typically generate short fragments, and require primers to be placed directly on areas of interest if longer regions are to be evaluated. Library preparation methods that use mechanical fragmentation or enzyme digestion can generate long fragments, but do not allow site-specific fragments to be directly generated. The method can be used to generate a long fragment HTPS library is as follows: Produced DNA fragments containing trigger regions are designed to bind at regions flanking template DNA in areas desired to be sequenced, such as in the introns surrounding the exons of one or more targeted genes. In one non-limiting embodiment, the distance between the probes could range from about 0.1 to about 10 kb, or any range having end points between 0.1 and 10 kb, inclusive. Once annealed, the template DNA/trigger-forming fragment hybrid is subjected to the appropriate enzyme mix required to cleave the DNA/cDNA at the trigger locations. The fragments are then separated from surrounding, larger fragments of DNA using standard size-selection techniques. For example, purification columns can be used as a size-selection matrix that allows DNA fragments below a certain cut-off (e.g. <10 kb) through but retains larger fragments in the size selection matrix.

Example 1: Generating a Targeted Double Stranded Break in DNA Using Trigger Nucleotide-Containing Probes (FIG. 3)

A 1312 bp fragment of the human CEBPA gene was amplified from genomic DNA using appropriate primers (one 20 nucleotides in length, the other 21 nucleotides in length) according to standard techniques followed by purification using Agencourt AMPure XP beads (Beckman Coulter Inc., Brea, Calif.) per the manufacturer's protocol. Trigger-containing DNA probes targeting the middle of the coding and non-coding strands of the CEBPA template were purchased from an oligonucleotide supplier. Sequences were designed to contain three dUTP residues per probe as triggers.

Equal concentrations of each probe were hybridized to CEBPA template in a reaction buffer, and then digested with a combination of 5 U of UDG, 10 U Endo IV and 5 U T7 Endo 1 (all from New England Biolabs inc., Ipswich, Mass.).

Figure 3A:
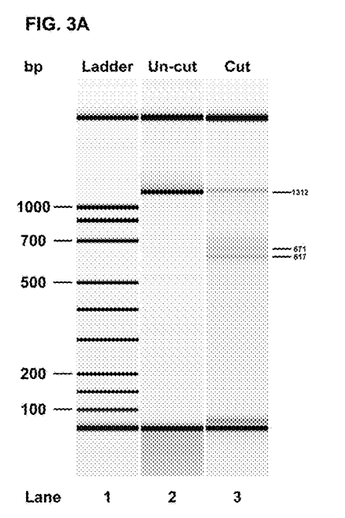
Figure 3B:
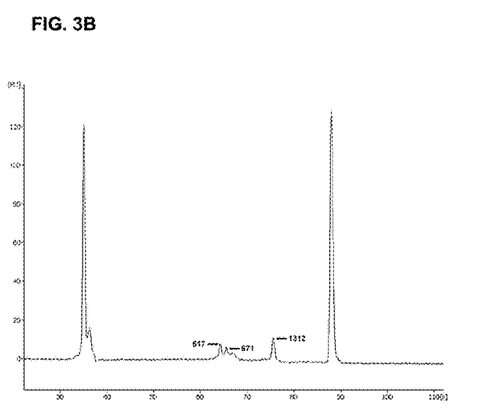

At the conclusion of the digestion, the sample was analyzed on an Agilent 2100 Bioanalyzer (Agilent Technologies, Santa Clara, Calif.) according to manufacturer's directions (FIG. 3). FIG. 3a is a gel image generated by the 2100 Bioanalyzer showing a DNA size marker ladder in lane 1, the unprocessed CEBPA template (approximately 1312 bp) in lane 2 and the products following template digestion in lane 3. The expected, trigger site-mediated double stranded break in template DNA was generated resulting in two fragments of approximately 617 and 671 bp also shown by peaks in the accompanying electropherogram tracing of lane 3 generated by the 2100 bioanalyzer (FIG. 3b). Buffer components, reaction conditions, concentrations of template, probes or enzymes can all be adjusted to produce the desired result.

The method can also be used to create a HTPS library by using it to directly sub-fragment longer fragments of DNA using the method described previously in FIG. 2. In some situations, it may be advantageous to create the small fragments required for most current HTPS technologies from a previously created longer fragment using direct cleavage rather than using PCR amplification, which frequently requires primers to be situated within the region to be sequenced. For example, the target sequence may not be amenable to internal primer design due to sequence constraints that do not allow multiple primer pairs to bind under a single set of reaction conditions. Alternatively, DNA sequence variants within the internal sequence might be present and inhibit primer binding. In these situations, it is easier to perform longer range PCR using a single primer set that flanks the region of interest, and then uniformly cleave the resultant product into sub-fragments of an appropriate size for subsequent sequencing. This approach, when used to create fragment libraries for high-throughput sequencing, can provide consistent read depth and coverage of regions that are difficult to sequence using standard, available library preparation technologies.

It is noted that New England Biolabs Inc. (Ipswich, Mass.) currently markets a product called fragmentase that is a mixture of enzymes that can be used in a similar manner without the use of trigger site generation. However, the fragmentase method has the disadvantage of being time-dependent; it will keep digesting DNA until the reaction is either stopped, or the DNA is gone. In addition, fragmentase may have bias depending on the nucleotide content of the target (that is, fragmentase works differently depending on GC nucleotide percentage with poor success on AT nucleotide-rich targets). The method describe here, which uses trigger site-based cleavage, has the advantage of being time-independent and has minimal/no sequence bias depending on the trigger used. As such, the technique requires minimal optimization and can be used successfully on a variety of different initial fragment sizes and DNA composition with the ability to digest multiple targets of different sizes and DNA content simultaneously.

Figure 4:
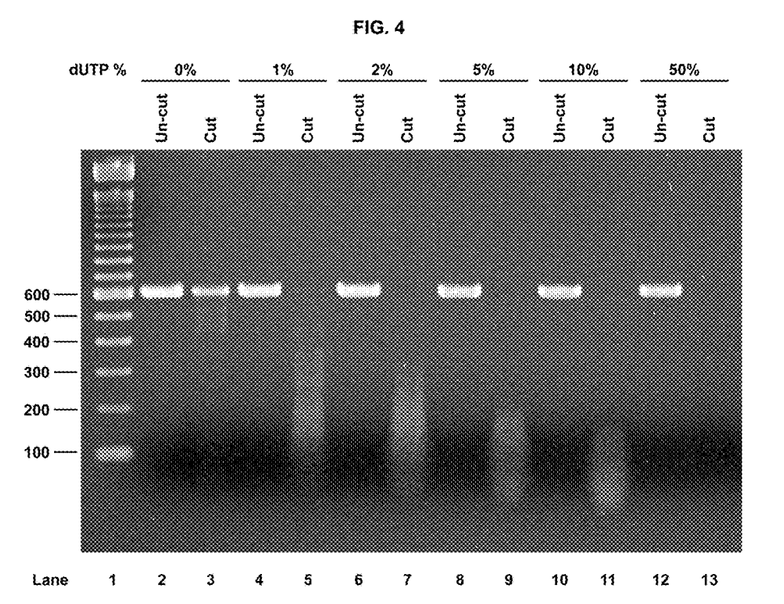
FIG. 4 illustrates results obtained by using the invention as per the embodiment described in FIG. 2.

Example 2: Using Quasi-Random Cleavage Trigger Nucleotide Incorporation and Digestion to Form Fragments of a Specific Average Size (FIG. 4)

PCR reactions were prepared using Phusion U Hot Start DNA Polymerase (Thermo Fisher Scientific Inc. Waltham, Mass.) according to manufacturer's protocol but containing dNTP mixes with 0-50% of the dTTP fraction replaced by dUTP. In this example, a 600 bp fragment of the gene, FLT3, was amplified and the resulting PCR product purified using Agencourt AMPure XP beads (Beckman Coulter Inc., Brea, Calif.) per the manufacturer's protocol. The purified fragments were digested with a combination of 5 U of UDG, 10 U Endo IV and 10 U T7 Endo 1 (all from New England Biolabs inc., Ipswich, Mass.). At the conclusion of the digestion, samples were analyzed on an agarose gel according to standard laboratory techniques (FIG. 4). The gel shows a portion of each purified sample pre- and post-digestion for each of the different dUTP concentrations tested. As the concentration of dUTP increases, so does the number of trigger sites incorporated into the amplified fragments which results in smaller average fragment sizes post-digestion (seen as DNA smears in lanes labeled "cut" in which dUTP was present). By adjusting the amount of trigger nucleotide in the initial PCR reaction mixture, fragments of any average size that is amenable to the desired downstream application can be generated.

Application for Negative Selection by Degradation of Non-Desirable DNA/cDNA.

Another application of the invention is to selectively digest regions of DNA that are not desirable, thereby enriching the desired regions for downstream applications. For example, when preparing libraries for HTPS of RNA (or cDNA), the relative abundance of each gene sequence is correlated to the expression level of that transcript in the cell/tissue being examined. This differs from sequencing DNA where there should be relatively equal copies of each sequence in the genome present (except in the case of aneuploidy). As such, when libraries are generated from RNA template for sequencing, a disproportionate number of transcripts are present for commonly expressed housekeeping genes, rRNA, and globin genes (specifically in blood). Genes expressed at low levels become underrepresented or missed entirely in sequencing results even though these transcripts are typically the ones that have the most clinical significance. Several strategies have been developed to enrich for rare transcripts, either by removal of abundant transcripts that have little clinical significance or by selecting for clinically relevant mRNA. However, these strategies use time consuming and costly techniques, typically bead selection with beads containing oligonucleotide sequences specific for the transcripts being selected, a process in which each unique sequence being targeted must be designed and attached to magnetic beads. Numerous target sequences are required to ensure efficient capture because any transcripts with sequence differences from that of the oligonucleotide probe will have reduced binding affinity. In certain bead-capture enrichment protocols, clinically relevant single nucleotide or other small sequence variants may be underrepresented in the resulting HTPS library due to a lack of specific probes. By using an embodiment of the method described here (Example 2), a probe library can be generated using a modified PCR reaction. This library can then be used per the method described in FIG. 1 and Example 1. This process is more cost- and time-effective than other techniques since it involves depletion of unwanted targets rather than enrichment of those desired, has no loss of novel transcripts, is adaptable to any sequence and can be multiplexed. Other embodiments of the technique could deplete wild-type transcripts of a gene to increase the sensitivity of detecting transcripts with mutations, deplete unwanted regions of DNA template or selectively remove species-specific transcripts/DNA from mixed specimens (which is common in HTPS of infectious organisms from specimens of human tissue).

The invention claimed is:
1. A method of processing DNA molecules comprising:
   creating a reaction mixture by binding at least one uracil-containing oligonucleotide to a precursor DNA containing a target sequence, the precursor DNA being a single-stranded DNA, each of the at least one uracil-containing oligonucleotides binding in sequence-specific fashion to a region adjacent the target sequence to form a uracil-containing duplex;
   treating the uracil-containing duplex with a first enzyme comprising uracil DNA glycosylase to remove the uracil base and to create an apyrimidinic site to form an apyrimidinic site-containing duplex;
   treating the apyrimidinic site-containing duplex with a second enzyme comprising endonuclease IV to create a nick at the apyrimidinic site to form a partial duplex, the precursor being intact opposite the nick; and treating the partial duplex with a third enzyme comprising T7 endonuclease I to cut the precursor DNA opposite the nick to produce a processed DNA.

2. The method according to claim 1 wherein each of the first enzyme, the second enzyme, and the third enzyme are added to the reaction mixture individually.

3. The method according to claim 1 wherein each of the first enzyme, the second enzyme, and the third enzyme are added to the reaction mixture simultaneously.

4. The method according to claim 1 wherein the uracil DNA glycosylase, endonuclease IV, and T7 endonuclease I are provided together as a kit.

5. The method according to claim 1, wherein the precursor DNA is selected from the group consisting of a genomic DNA, a cDNA, a plasmid, a PCR product, and a synthetic DNA.

6. The method according to claim 1, wherein the method yields at least one nucleic acid having a length of 0.1 kilobase to 10 kilobases.

7. A method of processing DNA comprising:
performing a polymerase chain reaction using a polymerase, at least one DNA primer, and a nucleotide mixture, on a precurser DNA containing a target sequence, the nucleotide mixture comprising a uracil-containing nucleotide, the polymerase being capable of incorporating uracil into a product DNA, each of the at least one DNA primers having sequence homology to a region adjacent the target sequence of the precursor DNA, the polymerase chain reaction forming a uracil-containing duplex;

treating the uracil-containing duplex with a first enzyme comprising uracil DNA glycosylase to remove the uracil base and to create an apyrimidinic site to form an apyrimidinic site-containing duplex;

treating the apyrimidinic site-containing duplex with a second enzyme comprising endonuclease IV to create a nick at the apyrimidinic site to form a partial duplex, the precursor DNA being intact opposite the nick; and treating the partial duplex with a third enzyme comprising T7 endonuclease I to cut the precursor DNA opposite the nick.

8. The method according to claim 7 wherein the nucleotide mixture contains a ratio of dTTP:dUTP of about 9999:1 to about 1:1.

9. The method according to claim 7, wherein the precursor DNA is selected from the group consisting of a genomic DNA, a cDNA, a plasmid, a PCR product, and a synthetic DNA.

10. The method according to claim 7, wherein the method yields at least one nucleic acid having a length of 0.1 kilobase to 10 kilobases.

* * * * *